United States Patent
Nagy et al.

(10) Patent No.: US 10,308,622 B2
(45) Date of Patent: Jun. 4, 2019

(54) LIQUID PHASE SELECTIVE OXIDATION TO EPOXIDES WITH MOLECULAR OXYGEN

(71) Applicant: Lyondell Chemical Technology, L.P., Houston, TX (US)

(72) Inventors: Sandor Nagy, Seabrook, TX (US); Barbara Kimmich, Houston, TX (US); Justin E. Turner, Conroe, TX (US); Nicholas Bruschi, Houston, TX (US); George R. Horvat, Houston, TX (US)

(73) Assignee: Lyondell Chemical Technology, L.P., Houston, TX (US)

(*) Notice: Subject to any disclaimer, the term of this patent is extended or adjusted under 35 U.S.C. 154(b) by 0 days.

(21) Appl. No.: 15/878,837

(22) Filed: Jan. 24, 2018

(65) Prior Publication Data

US 2018/0208569 A1    Jul. 26, 2018

Related U.S. Application Data

(60) Provisional application No. 62/449,868, filed on Jan. 24, 2017.

(51) Int. Cl.

| | |
|---|---|
| *C07D 301/06* | (2006.01) |
| *C07C 23/36* | (2006.01) |
| *B01J 23/50* | (2006.01) |
| *C07D 303/04* | (2006.01) |
| *C07C 23/44* | (2006.01) |
| *C07D 301/10* | (2006.01) |

(52) U.S. Cl.
CPC ............ *C07D 301/06* (2013.01); *B01J 23/50* (2013.01); *C07C 23/36* (2013.01); *C07C 23/44* (2013.01); *C07D 301/10* (2013.01); *C07D 303/04* (2013.01); *B01J 2231/72* (2013.01); *Y02P 20/52* (2015.11)

(58) Field of Classification Search
CPC .......... B01J 23/50; C07C 23/44; C07C 23/36; C07D 301/06; C07D 303/04
USPC ....................................................... 549/533
See application file for complete search history.

(56) References Cited

U.S. PATENT DOCUMENTS

| | | | |
|---|---|---|---|
| 5,145,968 A * | 9/1992 | Monnier ................ | B01J 23/66 546/281.7 |
| 5,625,084 A | 4/1997 | Pitchai et al. | |
| 5,703,254 A | 12/1997 | Gaffney et al. | |
| 5,861,519 A | 1/1999 | Kahn et al. | |
| 2009/0234145 A1* | 9/2009 | Corma Canos ........ | B01J 21/063 549/534 |
| 2012/0323026 A1* | 12/2012 | Lockemeyer .......... | B01J 27/051 549/536 |
| 2014/0248006 A1 | 9/2014 | Saha et al. | |

OTHER PUBLICATIONS

Betzemeier et al, Perfluorinated solvents—a Novel Reaction Medium in Organic Chemistry , ,Topics in Current Chemistry, 1999, vol. 206, p. 61-78. (Year: 1999).*
Klement et al , Transition Metal Catalyzed Oxidations in Perfluorinated Solvents, Communications, Angew. Chem. Int. Ed. Engl. 1997, 36, No. 13/14, p. 1454-1456. (Year: 1997).*
Ronald W. Millard, Oxygen Solubility, Rheology and Hemodynamics of Perfluorocarbon Emulsion Blood Substitutes, Artificial Cells, Blood Substitutes, and Biotechnology, 22:2, 1994, pp. 235-244.
A.M.A. Dias et al., Solubility of Oxygen in Liquid Perfluorocarbons, Fluid Phase Equilibria, 222-223, 2004, pp. 325-330.
Bodo Betzemeier et al., Oxidation Reactions in Perfluorinated Solvents, Peroxide Chemistry: Mechanistics and Preparative Aspects of Oxygen Transfer, 2000, Wiley-VCH Verlag GmbH, ISBNs: 3-527-27150-3 (Softcover); 3-527-60039-6 (Electronic), pp. 454-468.
Giancula Pozzi et al., Efficient Aerobic Epoxidation of Alkenes in Perfluorinated Solvents Catalysed by Chiral (Salen) Mn Complexes, Chemical Communincations, 1998, pp. 877-878.
Takahiro Iwahama et al., Epoxidation of Alkenes Using Dioxygen in the Presence of an Alcohol Catalyzed by N-Hydroxyphthalimide and Hexafluoroacetone without Any Metal Catalyst, Chemical Communications, 1999, pp. 727-728.
Qing Zhang et al., Gas-Phase Epoxidation of Propylene by Molecular Oxygen over Ag—Cu—Cl/BaCO3 Catalyst: Effects of Cu and Cl Loadings, Chinese Journal of Catalysis, vol. 38, 2017, pp. 65-72.
The International Search Report and Written Opinion for PCT/US2018/015004 dated Apr. 17, 2018.

* cited by examiner

*Primary Examiner* — Taylor V Oh

(57) ABSTRACT

The present disclosure relates to a method for effecting catalytic selective oxidation in liquid phase comprising a perfluorinated solvent and an olefinic compound with molecular oxygen to produce an epoxide. The method may provide enhanced selectivity to the epoxide of greater than 60%. The olefinic compound may be ethylene, propylene, butenes, 1-octene, butadiene, allyl chloride, allyl alcohol, styrene, and the like. The perfluorinated solvent may be perfluoro methyldecalin, perfluorodecalin, perfluoroperhydrophenanthrene, perfluoro (butyltetrahydrofuran), isomers thereof, or a combination thereof. In some embodiments, the method includes catalytically epoxidizing, in a liquid phase comprising a perfluorinated solvent, propylene with molecular oxygen to produce propylene oxide. A system for carrying out the method is also provided, the system comprising a source of a perfluorinated solvent, and a liquid phase reactor fluidly connected with the source, and configured for effecting catalytic selective oxidation, in a liquid phase comprising the perfluorinated solvent, of an olefinic compound with molecular oxygen to produce an epoxide.

20 Claims, No Drawings

LIQUID PHASE SELECTIVE OXIDATION TO EPOXIDES WITH MOLECULAR OXYGEN

CROSS-REFERENCE TO RELATED APPLICATIONS

This application claims the benefit of priority to U.S. Provisional Application No. 62/449,868 filed on Jan. 24, 2017, which is incorporated herein by reference in its entirety.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD OF THE INVENTION

This disclosure relates to liquid phase selective oxidation to epoxides with molecular oxygen; more specifically, this disclosure relates to systems and methods for liquid phase selective oxidation to epoxides with molecular oxygen in the presence of a high-boiling, non-reactive solvent; still more specifically, this disclosure relates to systems and methods for liquid phase selective oxidation to epoxides with molecular oxygen in the presence of a perfluorinated solvent.

BACKGROUND OF THE INVENTION

The liquid phase selective oxidation of olefins, such as propylene, to epoxides using oxygen sources other than molecular oxygen, like hydrogen peroxide, tert-butyl peroxide (TBHP), ethylbenzene peroxide (EBHP), and cumene hydroperoxide is known and can be performed by utilizing homogeneous and heterogeneous catalysts, such as molybdenum compounds or titanated silica, which can be used to produce epoxides along with one or more co-products. These coproducts, such as tert-butyl alcohol in the case of TBHP, or methylbenzyl alcohol in the case of EBHP, are not always desirable. It would be desirable to have a co-product-free process for producing epoxides, such as propylene oxide. Conceptually, this can be accomplished by utilizing molecular oxygen.

Gas phase epoxidation utilizing molecular oxygen, for example, gas phase epoxidation of ethylene in the presence of a silver-containing catalyst at 200-300° C., is known. However, epoxidation of olefins other than ethylene in the gas phase is difficult due to low process selectivity of the reaction associated with the presence of reactive hydrogen atoms in the allylic position to the double bond.

An ongoing need exists for systems and methods for selective epoxidation with molecular oxygen; desirably such systems and methods enable selective oxidation in the liquid phase, which selective oxidation may be continuous.

SUMMARY OF THE INVENTION

Herein disclosed is a method comprising: carrying out selective oxidation, in liquid phase, of an olefinic compound with molecular oxygen to produce an epoxide, wherein the liquid phase comprises a perfluorinated solvent, and wherein the selective oxidation is carried out in the presence of a catalyst. In embodiments, the perfluorinated solvent has a boiling point in the range of from about 80-300° C., at atmospheric pressure. Without limitation, in embodiments, the perfluorinated solvent is selected from the group consisting of perfluoro methyldecalin, perfluorodecalin, perfluoroperhydrophenanthrene, perfluoro(butyltetrahydrofuran) (FC-75), isomers thereof, and combinations thereof. In embodiments, the perfluorinated solvent is a nonreactive solvent.

In embodiments, selective oxidation to epoxide is carried out in the presence of a homogeneous catalyst, a heterogeneous catalyst, or both. In embodiments, selective oxidation to epoxide is carried out in the presence of a homogeneous catalyst. In embodiments, the homogeneous catalyst is selected from the group consisting of transition metal compounds comprising one or more component selected from the group consisting of complexes of manganese, molybdenum, tungsten, iron, chromium, nickel, cobalt, copper, ruthenium and combinations thereof. In embodiments, selective oxidation to epoxide is carried out in the presence of a heterogeneous catalyst. In embodiments, the heterogeneous catalyst comprises a support and a metal selected from the group consisting of silver, gold, copper, ruthenium, molybdenum, tungsten, and combinations thereof. In embodiments, the support comprises one or more component selected from the group consisting of metal oxides, alkaline earth carbonates, and phyllosilicates. In embodiments, the metal oxide is selected from the group consisting of alumina, silica titania, zirconia, and mixtures thereof. In embodiments, the alkaline earth carbonate comprises calcium carbonate. In embodiments, the phyllosilicate is selected from the group consisting of talc, kaolinite, pyrophyllite, and combinations thereof.

In embodiments, the olefinic compound is selected from the group consisting of ethylene, propylene, butenes, 1-octene, butadiene, allyl chloride, allyl alcohol, styrene, and combinations thereof. In embodiments, the olefinic compound comprises propylene. Without limitation, in embodiments, the olefinic compound comprises propylene, and the perfluorinated solvent is selected from the group consisting of perfluoro methyldecalin, perfluorodecalin, perfluoroperhydrophenanthrene, perfluoro(butyltetrahydrofuran), isomers thereof, and combinations thereof. In embodiments, the olefinic compound comprises propylene, and the perfluorinated solvent is selected from the group consisting of perfluorodecalin, perfluoro methyldecalin, and combinations thereof. In embodiments, the selective oxidation to epoxide is carried out in the presence of a heterogeneous catalyst. In embodiments, the heterogeneous catalyst is not shaped. In embodiments, the heterogeneous catalyst is shaped. In embodiments, the heterogeneous catalyst is in the form of a powder. In embodiments, the heterogeneous catalyst comprises a support, and the support comprises at least one component selected from the group consisting of phyllosilicates. In embodiments, the phyllosilicate is selected from the group consisting of talc, kaolinite, pyrophyllite, and combinations thereof. In embodiments, the heterogeneous catalyst comprises silver. In embodiments, the silver has an oxidation state of zero. In embodiments, the heterogeneous catalyst comprises from about 1 weight percent to about 70 weight percent silver. In embodiments, the catalyst further comprises a Group 1 metal salt. In embodiments, the Group 1 metal salt is potassium nitrate. In embodiments, the catalyst comprises from about 0.05 to about 10 weight percent of the Group 1 metal salt. In embodiments, the catalyst further comprises a promoter selected from the group consisting of rhenium, tungsten, zinc, nickel, gold, copper, sodium, potassium, lithium, rubidium, cesium, molybdenum, and combinations thereof.

In embodiments, carrying out selective oxidation comprises heating to a temperature in the range of from about 50-300° C. for a time period of at least 0.1 hour, at least 1 hour, at least 3 hours, or in the range of from about 0.1 hour to about 3 hours. In embodiments, the selectivity to the epoxide (selectivity defined as the mole percent of reacted olefinic compound converted to epoxide) provided by the herein disclosed method is greater than or equal to about 40%. In embodiments, the selectivity to the epoxide (selectivity defined as the mole percent of reacted olefinic compound converted to epoxide) provided by the herein disclosed method is greater than or equal to about 50%. In embodiments, the selectivity to the epoxide (selectivity defined as the mole percent of reacted olefinic compound converted to epoxide) provided by the herein disclosed method is greater than or equal to about 60%. In embodiments, the olefinic compound comprises propylene, and the epoxide comprises propylene oxide. In embodiments, at least a majority of the selective oxidation is carried out continuously. In embodiments, selective oxidation is carried out by supplying the olefinic compound and a gas comprising molecular oxygen into a reactor containing the perfluorinated solvent and equipped with a distillation section. In embodiments, the method further comprises continuously removing the epoxide to reduce byproduct formation.

Also disclosed herein is a method comprising: carrying out selective catalytic oxidation, in liquid phase, of propylene with molecular oxygen to produce propylene oxide, wherein the selective oxidation is carried out in the presence of a catalyst, and wherein the liquid phase comprises a perfluorinated solvent.

Also disclosed herein is a system comprising: a source of a perfluorinated solvent; and a liquid phase epoxidation reactor fluidly connected with the source of the perfluorinated solvent, and configured for carrying out selective oxidation, in the presence of a catalyst and in a liquid phase comprising the perfluorinated solvent, of an olefinic compound with molecular oxygen to produce an epoxide.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the detailed description is to be regarded as illustrative in nature and not restrictive.

DETAILED DESCRIPTION OF THE INVENTION

Herein disclosed are systems and methods for liquid phase epoxidation with molecular oxygen. It has been surprisingly discovered that perfluorinated solvents are particularly suitable for use as a reaction medium for liquid phase epoxidation reactions. Particularly suitable perfluorinated solvents may be high-boiling, non-reactive solvents capable of dissolving a high level of molecular oxygen.

The phrases 'selective oxidation to epoxides' and 'epoxidation' are used interchangeably herein.

Herein disclosed is a method of effecting selective oxidation, in the presence of a catalyst, of an olefinic compound with molecular oxygen in a liquid phase comprising a perfluoro hydrocarbon to produce an epoxide. The term 'epoxide' refers to a class of compounds of the formula:

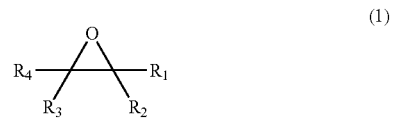

wherein R1, R2, and R3 are each independently hydrogen, alkyl, and R4 is hydrogen, alkyl, or aryl.

As indicated hereinabove, the selective oxidation of the olefinic compound according to this disclosure is carried out in the presence of a liquid phase comprising a perfluorinated solvent containing one or more perfluoro hydrocarbon. As used herein, 'perfluorinated' compounds are organofluorine compounds containing C—F bonds (no C—H bonds) and C—C bonds, which may also contain other heteroatoms. The perfluorinated solvent is nonreactive under epoxidation conditions. In embodiments, the solubility of molecular oxygen in the perfluorinated solvent is high.

The oxygen solubility level is a function of many variables, including pressure, temperature, presence of other components, etc., and is difficult to quantify. The solubility of oxygen in perfluorinated solvents is discussed, for example, in: Ronald W. Millard (1994) *Oxygen Solubility, Rheology and Hemodynamics of Perfluorocarbon Emulsion Blood Substitutes*, Artificial Cells, Blood Substitutes, and Biotechnology, 22:2, 235-244; and A. M. A. Dias, M. Freire, J. A. P. Coutinho, and I. M. Marrucho (2004) *Solubility of Oxygen in Liquid Perfluorocarbons*, Fluid Phase Equilibria, 222-223, 325-330. Without wishing to be limited by examples, in embodiments, 100 mL of the perfluorinated solvent dissolves at least 30 mL, 35 mL, 40 mL, 45 mL, or 50 mL of oxygen at 25° C. and atmospheric pressure. The Ostwald coefficient for solution volume can be defined as the volume of the dissolved gas divided by the volume of the liquid solution after equilibrium is reached. In embodiments, the perfluorinated solvent has an Ostwald coefficient, $L_{2,1}$ (T, p), at a solute partial pressure of 101.325 kPa, that is in the range of from about 0.4 to about 0.6, alternatively, greater than about 0.4, 0.45 or 0.5. In embodiments, the perfluorinated solvent has a solute mole fraction, $x_2$, at a solute partial pressure of 101.325 kPa, that is in the range of from about $3 \times 10^{-3}$ to about $5.5 \times 10^{-3}$, or greater than about $3.9 \times 10^{-3}$, $4 \times 10^{-3}$, or $4.2 \times 10^{-3}$.

In order to facilitate separation of the components of the reaction mixture, the liquid phase component(s) may be selected based on the difference in boiling points expected between the product of the epoxidation reaction and that of the component(s) of the liquid phase. In embodiments, the liquid phase/fluorinated solvent comprises one or more organofluorine compound having a boiling point above that of the epoxide being produced. In embodiments, the perfluorinated solvent has a boiling point of greater than or equal to about 80° C., 100° C., 110° C., 120° C., 130° C., 140° C., 150° C., or 160° C. In embodiments, the perfluorinated solvent has a boiling point, at atmospheric pressure, in the range of from about 80° C. to about 160° C., from about 100-250° C., from about 140-215° C., from about 100-160° C., from about 140-160° C., or from about 80-300° C., or any range therein.

As noted hereinabove, according to embodiments of this disclosure, the liquid phase comprises one or more perfluorinated hydrocarbons. In embodiments, the liquid phase comprises one or more organofluorine compound with the formula $C_xF_y$. In embodiments, the perfluorocarbon of the liquid phase comprises one or more hydrocarbon, including those with heteroatoms, wherein all C—H bonds have been replaced with C—F bonds. Such perfluorocarbon may have the formula $C_xF_yX_z$, where X is a halogen other than fluorine.

The perfluorinated hydrocarbon may be aliphatic or cycloaliphatic. Suitable perfluorocarbons include, without limitation, perfluoro methyldecalin, perfluorodecalin, perfluoroperhydrophenanthrene, perfluoro(butyltetrahydrofuran) [also known as FC-75], isomers thereof, and combinations thereof.

In embodiments, the olefinic compound, 'olefinic hydrocarbon,' olefin, or alkene which is epoxidized according to embodiments of this disclosure is any organic olefinic compound having at least one olefinic double bond having the general formula $R_1R_2C=CR_3R_4$, wherein $R_1$, $R_2$, $R_3$ and $R_4$ can be the same or different, substituted or non-substituted, and are each independently selected from hydrogen, alky, alkenyl, aryl, alkaryl, cycloalkyl, or alkylcycloalkyl, hydrocarbyl groups. In embodiments, $R_1$, $R_2$, $R_3$, and $R_4$ each have less than 30 carbon atoms. In embodiments, $R_1$, $R_2$, $R_3$, and $R_4$ each contain no more than 14 carbon atoms. In addition any of $R_1$, $R_2$, $R_3$, and $R_4$ can be linked together to form a substituted or non-substituted ring structure, such as cycloalkyl, cycloalkenyl or alkylcycloalkyl, cyclic hydrocarbyl, or aromatic ring group. Such substituted or non-substituted ring structure may, in embodiments, contain no more than 14 carbon atoms, or from 5 to 12 carbon atoms, in total. The olefinic compound may be straight-chain, branched-chain or cyclic. Cyclic olefinic compounds include monocyclic, bicyclic and polycyclic compounds. The olefinic compound may be mono-olefinic, di-olefinic or poly-olefinic. If more than one olefinic bond is present, the compound may be conjugated or non-conjugated. In embodiments, the olefinic compound may be substituted by one or more of a halide (e.g. Cl, F, Br, I), an ether group, an ester group, and/or an allylic hydroxyl.

In embodiments, the olefinic compound to be epoxidized is an aliphatic or alicyclic hydrocarbon containing from 2 to about 20 carbon atoms. In embodiment, the olefinic compound to be epoxidized contains a single double bond.

Examples of olefinic compounds which may be epoxidized according to this disclosure include, but are not limited to, ethylene, propylene, butenes, 1-octene, butadiene, allyl chloride, allyl alcohol, styrene, and combinations thereof. In embodiments, the olefin comprises propylene and the epoxide comprises propylene oxide.

Liquid phase epoxidation according to this disclosure is carried out in the presence of an oxidant (also referred to herein as an 'oxidizing agent'). According to this disclosure, the oxidizing agent is, comprises, or otherwise provides molecular oxygen ($O_2$). The molecular oxygen may be provided as pure or as a mixture with an inert diluent.

In embodiments, molecular oxygen and the olefinic compound are combined in a mixed gas phase prior to contact with the solvent. In embodiments, the olefinic compound and molecular oxygen are introduced separately into the reaction. The olefinic compound, molecular oxygen, or both may be introduced as a mixed gas phase comprising one or more diluent or carrier gas inert to the epoxidation, such as, without limitation, carbon dioxide, carbon monoxide, nitrogen, noble gas (e.g., helium, argon), and the like. The molar ratio of olefinic compound to oxygen in the reaction mixture may vary depending on the type of catalyst, the reaction temperature, the reaction pressure, the reaction mode (continuous type or batch type), and the like. In embodiments, the molar ratio of olefinic compound to oxygen is in the range of from about 1:100 to 100:1, or from about 1:30 to about 30:1.

In embodiments, liquid phase epoxidation according to this disclosure is carried out in the presence of any suitable epoxidation catalyst known to those of skill in the art. In embodiments, the epoxidation is carried out in the presence of a homogeneous catalyst, a heterogeneous catalyst, or both. In embodiments, the liquid phase epoxidation is carried out in the presence of a homogeneous catalyst. In embodiments, the homogeneous catalyst is selected from the group consisting of transition metal compounds comprising one or more component selected from the group consisting of complexes of manganese, molybdenum, tungsten, iron, chromium, nickel, cobalt, copper, ruthenium and combinations thereof. The term 'transition metal' represents metal atom(s) selected from the elements from scandium through zinc, yttrium through cadmium, and lutetium through mercury on the Periodic Table.

In embodiments, the epoxidation catalyst is a heterogeneous catalyst comprising a support material and a metal component. In embodiments, the metal component is selected from the group consisting of silver, gold, copper, ruthenium, and combinations thereof. In embodiments, the metal component is a noble metal, such as, without limitation, palladium, gold, platinum, silver, iridium, ruthenium, osmium or combinations thereof. In embodiments, the noble metal is silver. In embodiments, the silver is present within the epoxidation catalyst composition in the zero oxidation state (e.g., elemental silver). Alternatively, or in combination therewith, the silver may be present in a cationic oxidation state. When present in both the zero oxidation state and the cationic oxidation state, embodiments include more silver in the zero oxidation state than in the cationic oxidation state. It is further contemplated that the silver may be deposited on the support material as cationic silver and then may be reduced to elemental silver.

In embodiments, the epoxidation catalyst comprises a support known to those of skill in the art. In embodiments, the catalyst support comprises one or more component selected from the group consisting of metal oxides, alkaline earth carbonates, and phyllosilicates. In embodiments, the epoxidation catalyst comprises a metal oxide support. In embodiments, the metal oxide is selected from the group consisting of alumina, silica titania, zirconia, and mixtures thereof.

In embodiments, the epoxidation catalyst comprises an alkaline earth oxide support. In embodiments, the alkaline earth carbonate comprises calcium carbonate.

In embodiments, the epoxidation catalyst is substantially as described in U.S. Patent App. Ser. No. 62/363,401, filed Jul. 18, 2016, and entitled, "Epoxidation Processes and Catalysts for Use Therein", the disclosure of which is hereby incorporated herein in its entirety for all purposes not contrary to this disclosure. In embodiments, the epoxidation catalyst comprises a phyllosilicate support comprising a phyllosilicate solid component (i.e., phyllosilicate), which may be synonymously referred to herein as 'phyllosilicate', 'crystalline phyllosilicate', and 'layered silicate'. A wide variety of different phyllosilicates may be utilized as the support material. Phyllosilicates are generally layered silicates which can be characterized as platy or micaceous and are soft, flexible and elastic relative to other minerals. Phyllosilicates generally include tetrahedral sheets formed by oxygen atoms around silicon atoms with alternating octahedral or other polyhedral sheets with higher coordination numbers formed by divalent or trivalent cations and oxygen atoms of the silicate and hydroxide groups. The tetrahedral layer generally includes silica oxide where the vertex of the tetrahedron contains three oxygen atoms shared with other tetrahedral, forming interconnected six member rings extending outward. The octahedral or other polyhedral sheets are formed by the divalent and trivalent cations chelated with the apical oxygen atoms and the hydroxide which may be present in the center of the six member rings formed by the tetrahedral layer of the silica oxide. Phyllosilicates as disclosed herein are generally crystalline in the sense that the phyllosilicate has an ordered structure providing an x-ray diffraction pattern with distinct maxima.

The octahedral or polyhedral layer generally includes two major classifications: a brucite type structure including divalent cations with octahedral binding sites occupied with hydroxides and gibbsite type structure which include trivalent cations with every third cation site being unoccupied and the binding sites are occupied by hydroxides. These major classifications of the octahedral layer give rise to two major classes: dioctahedral and trioctahedral. For dioctahedral group phyllosilicates, the octahedral sheet contains trivalent cations such as aluminum cations. Within the dioctahedral group, the group has two structural types, t-o and t-o-t. The t-o structural type contains alternating layers of tetrahedral and octahedral sheets and is also known as a 1:1 dicotahedral group phyllosilicate. The t-o-t structural type contains alternating groups of a tetrahedral sheet, an octahedral sheet, and a tetrahedral sheet. The trioctahedral group phyllosilicate have octahedral sheets contains divalent cations such as iron or magnesium. Similar to the dioctahedral group phyllosilicates, a trioctahedral phyllosilicate may have either a t-o-t structural type or a t-o structural type as described above.

The phyllosilicates are generally divided into four groups of phyllosilicates: serpentine, clay mineral, mica, or chlorite groups. The serpentine group of phyllosilicates have the chemical formula $Mg_3Si_2O_5(OH)_4$ and include antigorite, chrysotile, and lizardite, for example. These serpentine groups of phyllosilicates generally exhibit monoclinic crystalline symmetry but may also exhibit either orthorhombic or hexagonal crystalline symmetry, for example. The mica group of phyllosilicates includes compounds with strong birefringence, have nearly perfect basal cleavage, and have monoclinic crystalline symmetry. These compounds have the general chemical formula: $X_2Y_4$-$6Z_8O_{20}(OH,F)_4$ wherein X is K, Na, Ca, or other Group 1 or Group 2 metals, Y is Al, Mg, or Fe, and Z is either Si or A but may also be $Fe^{3+}$ or Ti. The term 'Group 1 metal' represents metal atom(s) selected from lithium, sodium, potassium, rubidium, and cesium. The term 'Group 2 metal' represents metal atom(s) selected from beryllium, magnesium, calcium, strontium, and barium. Mica group phyllosilicates can be either dioctahedral or trioctahedral. Some non-limiting examples of mica group phyllosilicates include biotite, muscovite, phlogopite, lepidolite, margarite, phengite, hydro-muscovite, phologpite, zinnwaldite, and glauconite, for example. The chlorite group of phyllosilicates includes compounds which have the general formula: $(Mg,Fe)_3(Si,Al)_4O_{10}(OH)_2 \cdot (Mg,Fe)_3(OH)_6$ wherein one or more elements such as Mg, Fe, Ni, Mn, Li, Ca, or Zn have been substituted into the silicate lattice and have a t-o-t structure wherein the $(Mg, Fe)(OH)_6$ unit is spaced between each of the t-o-t repeats. These compounds are monoclinic but some also have triclinic polymorphs. Some non-limiting examples of chlorite phyllosilicates include baileychlore, chamosite, clinochlore, cookeite, donbassite, gonyerite, nimite, odinite, orthochamosite, pennantite, ripidolite, or sudoite, for example.

In some embodiments, the phyllosilicate is a clay mineral phyllosilicate. Clay mineral phyllosilicates are hydrous aluminum phyllosilicates with contain variable amounts of iron, magnesium, Group 1 metals, Group 2 metals, or other cations. The clay mineral phyllosilicates contain octahedral hydroxide sheets and tetrahedral silicate or alumina sheets which may be in either 1:1 tetrahedral to octahedral sheets or 2:1 tetrahedral to octahedral sheets. In these clay mineral phyllosilicates, the octahedral and tetrahedral sheets are linked by small cationic ions such as Mg or Al with the unshared oxygen atom of the silicate or alumina sheet pointing in the same direction (e.g., on the same side of the sheet). In order to adopt the appropriate bonding pattern, the tetrahedral sheet may become twisted or corrugated while the octahedral sheet is flattened. Clay mineral phyllosilicates may adopt a variety of crystal forms including but not limited to monoclinic and triclinic. Some non-limiting examples of clay mineral phyllosilicates include halloysite, kaolinite, illite, montmorillonite, vermiculite, talc, sepiolite, palygorskite, and pyrophyllite, for example.

In embodiments, the epoxidation catalyst comprises a clay mineral phyllosilicate support selected from the group consisting of talc, kaolinite, pyrophyllite, and combinations thereof. In some embodiments, the phyllosilicate solid component is talc. Talc is a trioctahedral phyllosilicate with a t - o - t structure and no net charge on either sheet, with a formula of $Mg_3Si_4O_{10}(OH)_2$. Talc has either a monoclinic or triclinic crystal symmetry. In certain embodiments, the support comprises a powdery talc.

In some embodiments, the phyllosilicate is kaolinite. Kaolinite is a dioctahedral phyllosilicate with a t-o structure, pH dependent charge, no interlayer cations, and a formula of $Al_2Si_2O_5(OH)_4$. Kaolinite is a part of a broader group of minerals known as kaolins which includes dickite, nacrite, halloysite, and kaolinite. Additionally, kaolinite has a triclinic crystal symmetry. In other embodiments, the phyllosilicate solid component is pyrophyllite. Pyrophyllite is a dioctahedral phyllosilicate with a t-o-t structure, no net charge, and a formula of $Al_2Si_4O_{10}(OH)_2$. Pyrophyllite has either a monoclinic or triclinic crystal symmetry.

The metal component may be incorporated into the catalyst as known to those of skill in the art. In embodiments, the metal component is incorporated into the catalyst by supporting the metal component on the support material to form the epoxidation catalyst composition. A wide variety of sources may be utilized to deposit the metal component onto the support material, such as metal salts. Some non-limiting examples of salts may include oxalates, acetates, citrates, malonates, complexing agents, stabilizing agents and combinations thereof, for example. Additional sources of metal components include those described in U.S. Pat. No. 5,861,519, which is hereby incorporated herein by reference in its entirety for all purposes not contrary to this disclosure. In embodiments, the source of the metal component includes metal oxides. In other embodiments, the source is a metal carboxylate. In yet other embodiments, the source includes a metal oxide with one or more stabilizing or complexing agents. For example, in embodiments, the stabilizing or complexing agent is a fatty acid or an amine containing alkyl group, such as ethylenediamine or ethanolamine.

In embodiments, the epoxidation catalyst comprises the metal component in an amount in a range of from 1 wt. % to 80 wt. %, from 10 wt. % to 70 wt. %, or from 40 wt. % to 60 wt. %, based on the total amount of epoxidation catalyst composition. In embodiments, the heterogeneous epoxidation catalyst comprises from about 10 wt. % to about 70 wt. % silver. However, in embodiments, the epoxidation catalyst composition includes a reduced loading of metal component. For example, in embodiments, the epoxidation catalyst composition includes the metal component in an amount in a range of from 1 wt. % to 50 wt. %, from 10 wt. % to 48 wt. %, from 40 wt. % to 47 wt. %, or less than 55 wt. %, based on the total amount of epoxidation catalyst composition.

In embodiments, the epoxidation catalyst composition further comprises a Group 1 metal salt. Non-limiting examples of Group 1 metal salts include Group 1 metal nitrate salts. In embodiments, the Group 1 metal nitrate salt comprises lithium nitrate, sodium nitrate, potassium nitrate, or a combination thereof. In embodiments, the metal salt is a potassium salt wherein the anion is a nitrogen oxyanion (i.e., an anion or negative ion which contains both nitrogen and oxygen atoms), such as nitrate and nitrite, or a carbon oxyanion (i.e., an anion or negative ion which contains both carbon and oxygen atoms), such as carbonate and bicarbonate, or precursors thereof (i.e., an anion capable of undergoing displacement or other chemical reaction and forming a nitrogen or carbon oxyanion under epoxidation or catalyst preparation or pretreatment conditions). In embodiments, the epoxidation catalyst comprises the Group 1 metal salt potassium nitrate, potassium nitrite, potassium carbonate, or a combination thereof. The catalyst may be treated with potassium salt as described in U.S. Pat. Nos. 5,861,519; 5,703,254; or 5,625,084, the disclosure of each of which is hereby incorporated herein in its entirety for all purposes not contrary to this disclosure.

When present in the epoxidation catalyst composition, the epoxidation catalyst composition may include the Group 1 metal salt in an amount in a range of from 0.01 wt. % to 10 wt. %, from 0.05 wt. % to 10 wt. %, from 0.5 wt. % to 8 wt. %, or from 1 wt. % to 6 wt. % based on the total weight of epoxidation catalyst. The amount will vary depending on such variables as the identity and concentration of reactants, the amount of catalyst metal (e.g., silver, gold) in the catalyst, the surface area and morphology of the support, the process conditions, etc. In embodiments, the epoxidation catalyst comprises a potassium salt, at a concentration range of the added potassium salt (calculated as the cation, K), of from about 0.15 to about 5 weight percent, from about 0.5 to about 3 weight percent, or from about 1.0 to about 2.5 weight percent, based on the total weight of the catalyst.

The epoxidation catalyst composition may further include an additional promoter or activator metal. In some embodiments, the additional promoter or activator metal is deposited on the support material concurrently with the metal component. In other embodiments, the additional promoter or activator metal is deposited on the support material after the deposition of the metal component.

The additional promoter may include a promoter metal, such as rhenium, molybdenum, tungsten, iron, nickel, copper, zinc, scandium, ytterbium, other lanthanoid metals or combinations thereof. In embodiments, the epoxidation catalyst comprises a promoter selected from the group consisting of rhenium, tungsten, zinc, nickel, gold, copper, sodium, potassium, lithium, rubidium, cesium, molybdenum, and combinations thereof. In embodiments, the promoter metal is rhenium. The term 'lanthanoid' represents metal atom(s) selected from the elements from lanthanide through ytterbium on the periodic table. In some embodiments, a commercially available salt of these metals may be used to prepare an epoxidation catalyst composition including such promoter metals. When present in the epoxidation catalyst composition, the epoxidation catalyst composition may include the additional promoter in an amount in a range of from 0.01 wt. % to 5 wt. %, from 0.5 wt. % to 2 wt. %, or from 0.1 wt. % to 1 wt. %, based on the total weight of epoxidation catalyst.

In embodiments, the heterogeneous catalyst is not shaped or 'formed'. In embodiments, the heterogeneous epoxidation catalyst is shaped or 'formed'. In embodiments, the heterogeneous epoxidation catalyst is in the form of a powder. Regardless of the support/carrier utilized, the catalyst may be shaped into particles, chunks, pieces, and the like. For example, for a fixed bed reactor, the catalyst may be formed into a desired shape, for example, in the form of spheres, pellets, cylinders, tablets, or rings. The catalyst may have any suitable dimensions as known in the art, for example, in the range of from about 2 nm to about 2 cm.

One or more components of the epoxidation catalyst composition may be calcined at an elevated temperature in the presence of air. The calcining temperature may be in a range of from about 150-800° C., from about 200-400° C., or from about 250-350° C., for example.

The epoxidation catalyst may be present in an amount effective to provide epoxidation. The olefin/catalyst ratio will vary depending on the application. For example, the olefin to catalyst ratio may be largely different for homogeneous vs. heterogeneous catalyst systems. However, by way of non-limiting example, the amount of epoxidation catalyst may be at least 0.00005 mole or 0.0001 mole of catalyst metal (e.g., elemental silver) per mole of olefinic compound (e.g., propylene). The upper limit thereof is not particularly limited, and a greater amount of epoxide may be produced if the amount of catalyst is increased. However, the upper limit of the amount of epoxidation catalyst may be adjusted by taking into consideration the cost of additional catalyst. In embodiments, the amount of epoxidation catalyst is not greater than 1 mole of catalyst metal (e.g., metallic silver) per mole of olefinic compound (e.g., propylene).

In embodiments, the olefinic compound and oxidant are introduced (e.g., bubbled) into a liquid phase epoxidation reactor containing the perfluorinated solvent liquid phase under conditions effective to accomplish at least partial epoxidation of the olefinic compound. The method may further comprise the introduction of one or more additives to the reaction mixture, the olefin, the epoxide or combinations thereof, as known to those of skill in the art. Non-limiting examples of additives include water, carbon dioxide, nitrogen containing compounds, $NO_x$ gases (e.g., NO and $NO_2$), organic halides, CO, $PH_3$, $SO_2$, $SO_3$ and combinations thereof.

In embodiments, the olefinic compound is introduced into the epoxidation reaction in an amount in a range of from 0.1 wt % to 50 wt %, from 1 wt % to 20 wt %, or from 2 wt % to 10 wt % based on the total weight of reaction mixture. In embodiments, the olefinic compound is present at a level of at least 0.1, 1, or higher, weight percent of the liquid phase. In embodiments, the oxygen is introduced into the epoxidation reaction in an amount in the range of from 1 wt % to 11 wt % from 2 wt % to 10 wt %, or from 4 wt % to 9 wt %, based on the total weight of reaction mixture. In embodiments, oxygen is introduced into the liquid phase epoxidation reactor at a level of at least 1, 5, or 10 weight percent of the liquid phase. In embodiments, the olefinic compound and the epoxidation catalyst composition are introduced to the reactor prior to or simultaneously with the introduction of oxygen.

The pressure of the liquid phase selective oxidation to epoxide will vary depending on the application. For example, the process pressure will depend on the process temperature, and the configuration, etc. The liquid phase selective oxidation to epoxide may be carried out at about atmospheric pressure. In embodiment, the liquid phase epoxidation is carried out at a pressure in the range of from about 0 psig (101.3 kPa) to about 500 psig (3447 kPa), from 0 psig (101.3 kPa) to about 450 psig (3204 kPa), or from 0 psig (101.3 kPa) to about 400 psig (2859 kPa). The epoxidation may be carried out at any suitable temperature depending on the reagents, the catalysts, and the perfluorinated solvent utilized. The perfluorinated solvent is a liquid at the temperature and pressure of reaction. In embodiments, the epoxidation is carried out at a temperature in the range of from about 50-300° C., from about 100-300° C., from about 200-300° C., or from about 150-250° C. In embodiments, selective oxidation comprises heating to a temperature in the range of from about 50-300° C. for a time period of at least 0.1 hour, at least 1 hour, at least 3 hours, or in the range of from about 0.1 hour to about 3 hours.

In embodiments, the epoxidation is carried out batchwise. In embodiments, the epoxidation is carried out continuously. In embodiments, at least a majority of the liquid phase epoxidation is carried out continuously. In embodiments, the liquid phase epoxidation is carried out in a continuous stirred tank reactor (CSTR), optionally with recycled solvent. In embodiments, the liquid phase epoxidation is carried out in a bubble column, evaporating, or trickle-bed reactor. In embodiments, the epoxidation is carried out in a reactive distillation reactor or section.

The herein-disclosed liquid phase epoxidation method may further comprise continuously, semi-continuously, or periodically removing the epoxide to reduce byproduct formation. Removal of the epoxide product may be effected via any means known to those of skill in the art. for example, epoxide (e.g., propylene oxide) can be removed from a top section of a distillation column combined with an evaporating or bubble column reactor.

In embodiments, the liquid phase epoxidation exhibits a conversion in the range of from 0.5-90%, from 5-70%, from 5-30%, or from 10-50%. The term 'conversion' refers to the percentage of input converted. As used herein, conversion is calculated via the following equation: conversion (%)=epoxide (wt.)/olefinic compound fed (wt.)*100. In embodiments, the selectivity to the epoxide is greater than or equal to about 40%. In embodiments, the selectivity to the epoxide is greater than or equal to about 50%. In embodiments, the selectivity to the epoxide is greater than or equal to about 60%. As used herein, the selectivity is defined as the mole percent of reacted olefinic compound converted to epoxide product.

The above methods can be further modified and optimized for preparative, pilot- or large-scale production, either batch or continuous, using the principles and techniques of process chemistry as applied by a person skilled in the art.

Also disclosed herein is a system for liquid phase epoxidation. In embodiments, the system comprises a source of a perfluorinated solvent as described hereinabove, and a reactor operable with a liquid phase comprising the perfluorinated solvent, and configured to effect selective oxidation of an olefinic compound with molecular oxygen to produce an epoxide.

The liquid phase epoxidation reactor may be any reactor known to those of skill in the art to be operable to contact an olefinic hydrocarbon/compound to be epoxidized with an oxidizing agent that is, comprises, or otherwise provides molecular oxygen, in the presence of an epoxidation catalyst and a liquid phase perfluorinated solvent of this disclosure under conditions (as described hereinabove) such that at least a portion of the olefinic hydrocarbon is converted to the corresponding epoxide. In embodiments, such a liquid phase epoxidation reactor may be selected from the group consisting of continuous stirred tank reactors (CSTRs), bubble column reactors, evaporating reactors. fixed-bed reactors, and reactive distillation reactors.

In embodiments, the liquid phase epoxidation reactor comprises one or more inlets for the introduction of the reagents (i.e., oxidant, olefinic compound to be epoxidized, perfluorinated solvent, catalyst) into the reactor, and one or more outlet ports for removing product (i.e., epoxide) therefrom. In embodiments, the system is configured for the introduction of gaseous oxidizing agent and olefinic compound into a volume of perfluorinated solvent in the liquid phase epoxidation reactor. For example, the gaseous oxidizing agent and gaseous olefinic compound may be bubbled into a reactor containing the perfluorinated solvent. The reactor may be a reactive distillation column or a reactive section of a distillation column in which the epoxidation is carried out. Reactive distillation is a unit operation in which chemical reaction and multi-component distillation are carried out simultaneously in the same vessel. The epoxidation catalyst may be contained within the reactor (e.g., within a reactive distillation section of a distillation column), or may be introduced with the reagents. Heterogeneous catalyst may be maintained in a reactive section of a reactor by any means known to those of skill in the art. For example, epoxidation catalyst may be held in place via catalyst packing as described in U.S. Patent App. No. 2014/0248006, which is hereby incorporated herein by reference in its entirety for all purposes not contrary to this disclosure.

The herein-disclosed liquid phase epoxidation system may further comprise apparatus for continuously, semi-continuously, or periodically removing the epoxide to reduce the formation of byproduct(s). The apparatus for removing epoxide product may be external to, or integrated with, the epoxidation reactor. For example, a reactive distillation column may comprise a reactive section in which epoxidation is effected, and a stripping section, which may be situated adjacent the reactive section, configured to separate the epoxide product from reagents or by-products.

In embodiments, reaction product removed from the epoxidation reactor may be treated, as known to those of skill in the art, to separate the product epoxide therefrom. In embodiments, such as in applications utilizing a CSTR, perfluorinated solvent may be recycled.

The system and method of this disclosure provide for liquid phase epoxidation of olefins with molecular oxygen via utilization of perfluoro hydrocarbons as solvents therefor. The epoxidation catalyst employed in the liquid phase epoxidation can be selected from homogeneous systems (e.g., Mn, Cu, Mo, W, Fe complexes), or heterogeneous systems (e.g., supported Ag, Cu, Ru or Au). In embodiments, a supported silver catalyst is employed for the liquid phase epoxidation with molecular oxygen. Without wishing to be limited by theory, liquid phase epoxidation may result in a higher selectivity of oxidation toward epoxides due to a reduced number of radical processes relative to conventional gas phase epoxidation in the presence of molecular oxygen.

EXAMPLES

Example 1

Liquid Phase Epoxidation of 1-Octene with Molecular Oxygen

Experiments were performed to study liquid phase epoxidation in the presence of perfluorinated solvents. Thirty milliliters (58 g) of perfluorodecalin and 4 mL (2.84 g) of 1-octene were introduced into a 125 mL stainless steel autoclave along with 0.5 g of silver catalyst supported on Talc (C-95 AMTAL, available from the American Talc Company in Allamore, Tex.); 57% Ag) and post-treated with $KNO_3$. The reactor was purged with 8% $O_2$ in nitrogen, and then pressurized to 500 psig with the same gas. The closed reactor was heated, with stirring at 40 rpm, to 200° C. After 3 hours at 200° C., the reactor was cooled, depressurized and de-inventoried, resulting in about 32 grams of a colorless perfluorinated solvent phase ('perfluorodecane phase'), along with a small (~2 mL) second layer of light yellow phase ('octene phase'). Gas chromatographic (GC) analysis indicated the formation of 1,2-epoxyoctane as the main reaction product. Based on a rough estimate, at ~5% conversion the 1,2-epoxyoctane selectivity was greater than 60%. Table 1 provides the results of the GC analysis.

TABLE 1

GC Analysis Results of Example 1

| Component | Perfluorodecane phase, % | Octene phase, % |
|---|---|---|
| Perfluorodecane | 96.1 | 12 |
| 1-Octene | 2.6 | 80 |
| 1,2-Epoxyoctane | 0.07 | 4.4 |
| Heptanal | 0.01 | 0.7 |
| 1-Octen-3-one | 0.01 | 0.7 |
| 1-Octen-3-ol | 0.003 | 0.6 |
| 2-Octen-1-ol | 0.003 | 1.0 |

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A method comprising: carrying out selective oxidation to epoxide, in liquid phase, of an olefinic compound with molecular oxygen to produce an epoxide, wherein the selective oxidation is carried out in the presence of a catalyst, and wherein the liquid phase comprises a perfluorinated solvent.

B: A method comprising: carrying out selective oxidation, in liquid phase, of propylene with molecular oxygen to produce propylene oxide, wherein the selective oxidation is carried out in the presence of a catalyst, and wherein the liquid phase comprises a perfluorinated solvent.

C: A system comprising: a source of a perfluorinated solvent; and a liquid phase reactor fluidly connected with the source of the perfluorinated solvent, and configured for effecting selective oxidation, in a liquid phase comprising the perfluorinated solvent, of an olefinic compound with molecular oxygen to produce an epoxide, wherein the selective oxidation is effected in the presence of a catalyst Each of embodiments A, B and C may have one or more of the following additional elements: Element 1: wherein the perfluorinated solvent has a boiling point of greater than or equal to about 50° C. Element 2: wherein the perfluorinated solvent is selected from the group consisting of perfluoro methyldecalin, perfluorodecalin, perfluoroperhydrophenanthrene, perfluoro(butyltetrahydrofuran) (FC-75), isomers thereof, and combinations thereof. Element 3: wherein the perfluorinated solvent is a nonreactive solvent, and wherein 100 mL of the perfluorinated solvent dissolves at least 35 mL, 40 mL, or 45 mL of oxygen at 25° C. and atmospheric pressure. Element 4: wherein selective oxidation is carried out in the presence of a homogeneous catalyst, a heterogeneous catalyst, or both. Element 5: wherein selective oxidation is carried out in the presence of a homogeneous catalyst, and wherein the homogeneous catalyst is selected from the group consisting of transition metal compounds comprising one or more component selected from the group consisting of complexes of manganese, molybdenum, tungsten, iron, chromium, nickel, cobalt, copper, ruthenium and combinations thereof. Element 6: wherein selective oxidation is carried out in the presence of a heterogeneous catalyst, and wherein the heterogeneous catalyst comprises a support and a metal selected from the group consisting of silver, gold, copper, ruthenium, and combinations thereof. Element 7: wherein selective oxidation is carried out in the presence of a heterogeneous catalyst comprising a support, and wherein the support comprises one or more component selected from the group consisting of metal oxides, alkaline earth carbonates, and phyllosilicates. Element 8: wherein selective oxidation is carried out in the presence of a heterogeneous catalyst comprising a metal oxide support, and wherein the metal oxide support is selected from the group consisting of alumina, silica titania, zirconia, and mixtures thereof. Element 9: wherein selective oxidation is carried out in the presence of a heterogeneous catalyst comprising an alkaline earth carbonate support, and wherein the alkaline earth carbonate comprises calcium carbonate. Element 10: wherein selective oxidation is carried out in the presence of a heterogeneous catalyst comprising a phyllosilicate support, and wherein the phyllosilicate support is selected from the group consisting of talc, kaolinite, pyrophyllite, and combinations thereof. Element 11: wherein the olefinic compound is selected from the group consisting of ethylene, propylene, butenes, 1-octene, butadiene, allyl chloride, allyl alcohol, styrene, and combinations thereof. Element 12: wherein the olefinic compound comprises propylene. Element 13: wherein the olefinic compound comprises propylene, and wherein the perfluorinated solvent is selected from the group consisting of perfluoro methyldecalin, perfluorodecalin, perfluoroperhydrophenanthrene, perfluoro (butyltetrahydrofuran) (FC-75), isomers thereof, and combinations thereof. Element 14: wherein the olefinic compound comprises propylene, and wherein the perfluorinated solvent is selected from the group consisting of perfluorodecalin, perfluoro methyldecalin, and combinations thereof. Element 15: wherein the selective oxidation is carried out in the presence of a heterogeneous catalyst. Element 16: wherein the selective oxidation is carried out in the presence of a heterogeneous catalyst, and wherein the heterogeneous catalyst is not shaped. Element 17: wherein the selective oxidation is carried out in the presence of a heterogeneous catalyst, and wherein the heterogeneous catalyst is in the form of a powder. Element 18: wherein the selective oxidation is carried out in the presence of a heterogeneous catalyst, and wherein the heterogeneous catalyst is shaped. Element 19: wherein the selective oxidation is carried out in the presence of a heterogeneous catalyst, and wherein the heterogeneous catalyst comprises silver. Element 20: wherein the selective oxidation is carried out in the presence of a heterogeneous catalyst comprising silver, and wherein the silver has an oxidation state of zero. Element 21: wherein the selective oxidation is carried out in the presence of a heterogeneous catalyst comprising from about 10 weight percent to about 70 weight percent elemental silver. Element 22: wherein the selective oxidation is carried out in the presence of a heterogeneous catalyst, and wherein the heterogeneous catalyst further comprises a Group 1 metal salt. Element 23: wherein the selective oxidation is carried out in the presence of a heterogeneous catalyst, and wherein the catalyst further comprises potassium nitrate. Element 24: wherein the selective oxidation is carried out in the presence of a heterogeneous catalyst, and wherein the catalyst further comprises from about 0.05 to about 10 weight percent of a Group 1 metal salt. Element 25: wherein the selective oxidation is carried out in the presence of a heterogeneous catalyst, and wherein the catalyst further comprises from about 0.05 to about 10 weight percent of a Group 1 metal salt. Element 26: wherein the selective oxidation is carried out in the presence of a heterogeneous catalyst, wherein the catalyst further comprises from about 0.05 to about 10 weight percent of a Group 1 metal salt, and wherein the catalyst further comprises a promoter selected from the group consisting of rhenium, tungsten, zinc, nickel, gold, copper, sodium, potassium, lithium, rubidium, cesium, molybdenum, and combinations thereof. Element 27: wherein selective oxidation comprises heating to a temperature of at least 100° C., 200° C., or 300° C. for a time period of at least 0.1 hour, 1 hour, or 3 hours. Element 28: wherein the selectivity to the epoxide (selectivity defined as the mole percent of reacted olefinic compound converted to epoxide) is greater than or equal to about 40%, 50%, or 60%. Element 29: wherein the olefinic compound comprises propylene, and wherein the epoxide comprises propylene oxide. Element 30: wherein at least a majority of the selective oxidation to epoxide is carried out continuously. Element 31: wherein selective oxidation is carried out by bubbling the olefinic compound and an oxidant that provides molecular oxygen into a reactor containing the perfluorinated solvent and equipped with a distillation section. Element 32: further comprising continuously removing the epoxide to reduce byproduct formation.

While certain embodiments of the disclosure have been shown and described, modifications thereof can be made by one skilled in the art without departing from the teachings of this disclosure. The embodiments described herein are exemplary only, and are not intended to be limiting. Many variations and modifications of the disclosure are possible and are within the scope of the same.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the detailed description of the disclosure. The disclosures of all patents, patent applications, and publications cited herein are hereby incorporated by reference.

What is claimed is:

1. A method comprising:
carrying out selective oxidation, in liquid phase, of an olefinic compound with molecular oxygen to produce an epoxide, wherein the selective oxidation is carried out in the presence of an epoxidation catalyst, and wherein the epoxidation catalyst comprises more than 50 wt. % to 80 wt. % of a metal component, and wherein the liquid phase comprises a perfluorinated solvent, and
wherein the molar ratio of olefinic compound to molecular oxygen ranges from about 1:100 to 100:1.

2. The method of claim 1, wherein the perfluorinated solvent has a boiling point of greater than or equal to about 50° C.

3. The method of claim 1, wherein the perfluorinated solvent is selected from the group consisting of perfluoro methyldecalin, perfluorodecalin, perfluoroperhydrophenanthrene, perfluoro(butyltetrahydrofuran), isomers thereof, and combinations thereof.

4. The method of claim 1, wherein the selective oxidation is carried out in the presence of a homogeneous epoxidation catalyst, wherein the homogenous epoxidation catalyst is a transition metal compound comprising one or more component selected from the group consisting of complexes of manganese, molybdenum, tungsten, iron, chromium, nickel, cobalt, copper, ruthenium and combinations thereof.

5. The method of claim 1, wherein the selective oxidation is carried out in the presence of a heterogeneous epoxidation catalyst comprising a support and the metal component is selected from the group consisting of silver, gold, copper, ruthenium, and combinations thereof.

6. The method of claim 5, wherein the support comprises one or more component selected from the group consisting of metal oxides, alkaline earth carbonates, and phyllosilicates.

7. The method of claim 6, wherein the metal oxide is selected from the group consisting of alumina, silica titania, zirconia, and mixtures thereof.

8. The method of claim 6, wherein the alkaline earth carbonate comprises calcium carbonate.

9. The method of claim 6, wherein the phyllosilicate is selected from the group consisting of talc, kaolinite, pyrophyllite, and combinations thereof.

10. The method of claim 1, wherein the olefinic compound is selected from the group consisting of ethylene, propylene, butenes, 1-octene, butadiene, allyl chloride, allyl alcohol, styrene, and combinations thereof.

11. The method of claim 1, wherein the perfluorinated solvent is selected from the group consisting of perfluoro methyldecalin, perfluorodecalin, perfluoroperhydrophenanthrene, perfluoro(butyltetrahydrofuran), isomers thereof, and combinations thereof.

12. The method of claim 1, wherein the selective oxidation is carried out in the presence of a heterogeneous epoxidation catalyst comprising a support, and wherein the support comprises at least one component selected from the group consisting of phyllosilicates.

13. The method of claim 12, wherein the phyllosilicate is selected from the group consisting of talc, kaolinite, pyrophyllite, and combinations thereof.

14. The method of claim 12, wherein the heterogeneous epoxidation catalyst comprises silver.

15. The method of claim 1, wherein the selectivity to the epoxide is greater than or equal to about 40%.

16. The method of claim 1, wherein at least a majority of the selective oxidation to epoxide is carried out continuously.

17. The method of claim 1, wherein the selective oxidation is carried out by bubbling the olefinic compound and an oxidant that provides molecular oxygen into a reactor containing the perfluorinated solvent and equipped with a distillation section.

18. The method of claim 1 further comprising continuously removing the epoxide to reduce byproduct formation.

19. A method comprising:

carrying out selective oxidation, in liquid phase, of propylene with molecular oxygen to produce propylene oxide, wherein the selective oxidation is carried out in the presence of an epoxidation catalyst, and wherein the epoxidation catalyst comprises more than 50 wt. % to 80 wt. % of a metal component, and wherein the liquid phase comprises a perfluorinated solvent, wherein the molar ratio of propylene to molecular oxygen ranges from about 1:100 to 100:1.

20. A system comprising:

a source of a perfluorinated solvent; and a liquid phase reactor fluidly connected with the source of the perfluorinated solvent, and configured for effecting selective oxidation, in a liquid phase comprising the perfluorinated solvent, of an olefinic compound with molecular oxygen to produce an epoxide, wherein the selective oxidation is effected in the presence of an epoxidation catalyst, wherein the epoxidation catalyst comprises more than 50 wt. % to 80 wt. % of a metal component, and wherein the molar ratio of olefinic compound to molecular oxygen ranges from about 1:100 to 100:1.

* * * * *

UNITED STATES PATENT AND TRADEMARK OFFICE
CERTIFICATE OF CORRECTION

PATENT NO. : 10,308,622 B2
APPLICATION NO. : 15/878837
DATED : June 4, 2019
INVENTOR(S) : Nagy et al.

It is certified that error appears in the above-identified patent and that said Letters Patent is hereby corrected as shown below:

On the Title Page

Column 2, Item (56), Line 2, after "Chemistry," delete ","
Column 2, Item (56), Line 17, delete "Giancula" and insert -- Gianluca --
Column 2, Item (56), Line 19, delete "Communincations" and insert -- Communications, --

In the Specification

In Column 7, Line 27, delete "dicotahedral" and insert -- dioctahedral --
In Column 7, Line 58, delete "phologpite," and insert -- phlogopite, --
In Column 14, Line 28, after "catalyst" insert -- . --

Signed and Sealed this
Twenty-sixth Day of July, 2022

Katherine Kelly Vidal
*Director of the United States Patent and Trademark Office*